US010249040B2

(12) United States Patent  
Govindjee et al.

(10) Patent No.: US 10,249,040 B2  
(45) Date of Patent: *Apr. 2, 2019

(54) DIGITAL DATA PROCESSING FOR DIAGNOSIS OF A SUBJECT

(71) Applicant: International Business Machines Corporation, Armonk, NY (US)

(72) Inventors: Anita Govindjee, Ithaca, NY (US); Lakshminarayanan Krishnamurthy, Round Rock, TX (US); Niyati Parameswaran, Santa Clara, CA (US); Shanker Parameswaran, Mumbai (IN)

(73) Assignee: International Business Machines Corporation, Armonk, NY (US)

(*) Notice: Subject to any disclaimer, the term of this patent is extended or adjusted under 35 U.S.C. 154(b) by 32 days.

This patent is subject to a terminal disclaimer.

(21) Appl. No.: 15/356,876

(22) Filed: Nov. 21, 2016

(65) Prior Publication Data

US 2018/0144470 A1    May 24, 2018

(51) Int. Cl.
*G06T 7/00* (2017.01)
*A61B 3/00* (2006.01)
(Continued)

(52) U.S. Cl.
CPC .......... *G06T 7/0014* (2013.01); *A61B 3/0025* (2013.01); *A61B 5/0006* (2013.01); (Continued)

(58) Field of Classification Search
CPC ... G06T 7/0012; G06T 7/0014; G06T 7/0016; G06T 7/13; G06T 7/155; G06T 7/50; (Continued)

(56) References Cited

U.S. PATENT DOCUMENTS 8,923,585 B1* 12/2014 Peleg ............... A61B 5/004  
382/128  
2014/0147931 A1    5/2014 Chen

FOREIGN PATENT DOCUMENTS

WO    2007130673 A2    11/2007  
WO    2008031226 A1    3/2008  
(Continued)

OTHER PUBLICATIONS

Potocnik et al., The XUltra Project—Automated Analysis of Ovarian Ultrasound Images, Proceedings of the 15th IEEE Symposium on Computer-Based Medical Systems, 2002.

Cigale et al., Segmentation of Ovarian Ultrasound Images Using Cellular Neural Networks, International journal of pattern recognition and artificial intelligence, vol. 18, issue 04, Jun. 2004.

Kumar et al., Segmentation of Polycystic Ovary in Ultrasound Images, 2nd International Conference on Current Trends in Engineering and Technology, Jul. 8, 2014.

(Continued)

*Primary Examiner* — Andrew W Johns  
(74) *Attorney, Agent, or Firm* — Lieberman & Brandsdorfer, LLC

(57) ABSTRACT

Embodiments relate to digital image processing for diagnosis of a subject. More specifically, the embodiments relate to automation of diagnoses through data interpretation. An image is acquired from the subject. Elements are recognized within the image based on morphological features. The image is compared to learned data. Based on the comparison, a probability of a potential diagnosis(es) is calculated. A diagnosis of the subject is determined based on the potential diagnosis(es) and the calculated probability. The diagnosis may be changed based on a new image acquired from the subject.

20 Claims, 10 Drawing Sheets

(51) Int. Cl.
*A61B 6/00* (2006.01)
*A61B 8/08* (2006.01)
*A61B 5/00* (2006.01)
*A61B 5/0476* (2006.01)
*A61B 5/055* (2006.01)

(52) U.S. Cl.
CPC .......... *A61B 5/0042* (2013.01); *A61B 5/0476* (2013.01); *A61B 5/055* (2013.01); *A61B 5/4094* (2013.01); *A61B 5/7246* (2013.01); *A61B 5/7267* (2013.01); *A61B 5/7275* (2013.01); *A61B 5/742* (2013.01); *A61B 6/5217* (2013.01); *A61B 8/5223* (2013.01); *A61B 5/4325* (2013.01); *G06T 2207/10088* (2013.01); *G06T 2207/10101* (2013.01); *G06T 2207/10104* (2013.01); *G06T 2207/10108* (2013.01); *G06T 2207/10116* (2013.01); *G06T 2207/30016* (2013.01)

(58) Field of Classification Search
CPC ........... G06T 2207/20036; G06T 2207/20076; G06K 9/46; G06K 9/4604; G06K 9/4609; G06K 9/6201; G06K 9/6202; G06K 9/6215; A61B 5/7282; A61B 6/5217; A61B 8/5223
See application file for complete search history.

(56) References Cited

FOREIGN PATENT DOCUMENTS

| | | |
|---|---|---|
| WO | 2008066655 A2 | 6/2008 |
| WO | 2009125936 A2 | 10/2009 |
| WO | 2011157579 A1 | 12/2011 |

OTHER PUBLICATIONS

Sitheswaran et al., An Effective Automated System in Follicle Identification for Polycystic Ovary Syndrome Using Ultrasound Images, International Conference on Electronics and Communication System, 2014.

Fasih et al., Cellular Neural Networks-Based Genetic Algorithm for Optimizing the Behavior of an Unstructured Robot, International Journal of Computational Intelligence Systems 2(2), Jun. 2009.

Pedersen et al, Segmentation of Speckle-Reduced 3D Medical Ultrasound Images, IEEE International Ultrasonics Symposium Proceedings, 2008.

Park et al., Reduced Speckle Noise on Medical Ultrasound Images Using Cellular Neural Network, Proceedings of the 29th Annual International Conference of the IEEE EMBS cite Internationale, France, Aug. 23-26, 2007.

Tang, Edge Detection and Image Segmentation Based on Cellular Neural Network, 3rd International Conference on Bioinformatics and Biomedical Engineering, 2009.

List of IBM Patents or Applications Treated as Related, Nov. 2016.

\* cited by examiner

DIGITAL DATA PROCESSING FOR DIAGNOSIS OF A SUBJECT

BACKGROUND

The present embodiments relate to digital data processing for diagnosis of a subject. More specifically, the embodiments relate to automation of diagnoses through data interpretation.

The medical field continues to prefer non-invasive procedures to determine indicators for pathology identification and normalcy confirmation. Non-invasive procedures provide optimal subject comfort and limit harmful side effects. One popular non-invasive procedure is medical imaging of the subject, such as x-rays, ultrasound, and magnetic resonance imaging (MRI). The use of ultrasound and MRI technology mitigates or eliminates exposure to radiation while producing images of internal organs. For example, ultrasound imaging is used to produce images of internal organs of a subject by using sound waves. It is understood that medical images are subject to interpretation that is generally conducted by a trained Radiologist. Accordingly, imaging techniques are dependent on manual inspection and analysis which causes severe time overheads and are subject to interpretation which can lead to differences in diagnosis.

Another non-invasive medical procedure is electroencephalography (EEG), which is used to determine electrical activity of the brain to help diagnose epilepsy and forecast seizures. Forecasting seizures is important in order to warn the subject to avoid potentially dangerous activities, such as driving. Similar to medical imaging techniques, the EEG output is also subject to interpretation by a medical professional, which leads to varying analysis, and in one embodiment predictions. For example, in order to predict the seizures throughout the day, the EEG would have to be constantly monitored leading to an unmanageable time overhead.

From a health perspective, non-invasive procedures and medical evaluation processes, such as medical imaging and EEGs, may be preferred for diagnosis of a subject. However, as articulated above, such procedures, and more specifically, the output of such procedures is subject to interpretation. Any time a person is involved in such interpretations there is overhead and subjectivity, with overhead leading to an increase in cost(s), and subjectivity leading to perhaps different diagnoses.

SUMMARY

A system, computer program product, and method are provided to digitally process data in support of a medical diagnosis.

In one aspect, a computer system is provided with a processing unit in communication with a memory, and a functional unit in communication with the processing unit. The functional tool has an image diagnostic tool to determine a diagnosis. The image diagnostic tool captures an image. Within the image, a morphological feature of an element is recognized. The recognized morphological feature within the first image is compared to a previously recognized morphological feature of the element within at least one image. The image diagnostic tool determines a probability based on the comparison. The comparison and probability are used to create a diagnosis. The image diagnostic tool uses the recognized morphological feature, diagnosis, and probability to convert the image to a diagnostic image. More specifically, the diagnostic image is a visual representation of the diagnosis.

In another aspect, a computer program product is provided to determine a diagnosis. The computer program product includes a computer readable storage device with embodied program code that is configured to be executed by a processing unit. More specifically, program code is provided to capture an image and recognize a morphological feature of an element within the image. The recognized morphological feature within the first image is compared to a previously recognized morphological feature of the element within at least one image. Based on the comparison, program code determines a probability. The comparison and probability are used by the program code to create a diagnosis. Program code uses the recognized morphological feature, diagnosis, and probability to convert the image to a diagnostic image. More specifically, the diagnostic image is a visual representation of the diagnosis.

In yet another aspect, a method to is provided to determine a diagnosis. An image is captured and within the image a morphological feature of an element is recognized. The recognized morphological feature within the first image is compared to a previously recognized morphological feature of the element within at least one image. Based on the comparison a probability is determined. The comparison and probability are used to create a diagnosis. The recognized morphological feature, diagnosis, and probability are used to convert the image to a diagnostic image. More specifically, the diagnostic image is a visual representation of the diagnosis.

These and other features and advantages will become apparent from the following detailed description of the presently preferred embodiment(s), taken in conjunction with the accompanying drawings.

BRIEF DESCRIPTION OF THE SEVERAL VIEWS OF THE DRAWINGS

The subject matter which is regarded as embodiments is particularly pointed out and distinctly claimed in the claims at the conclusion of the specification. The forgoing and other features, and advantages of the embodiments are apparent from the following detailed description taken in conjunction with the accompanying drawings in which:

DETAILED DESCRIPTION

It will be readily understood that the components of the present embodiments, as generally described and illustrated in the Figures herein, may be arranged and designed in a wide variety of different configurations. Thus, the following detailed description of the embodiments of the apparatus, system, and method of the present embodiments, as presented in the Figures, is not intended to limit the scope of the embodiments, as claimed, but is merely representative of selected embodiments.

Reference throughout this specification to "a select embodiment," "one embodiment," or "an embodiment" means that a particular feature, structure, or characteristic described in connection with the embodiment is included in at least one embodiment of the present embodiments. Thus, appearances of the phrases "a select embodiment," "in one embodiment," or "in an embodiment" in various places throughout this specification are not necessarily referring to the same embodiment.

The illustrated embodiments will be best understood by reference to the drawings, wherein like parts are designated by like numerals throughout. The following description is intended only by way of example, and simply illustrates certain selected embodiments of devices, systems, and processes that are consistent with the embodiments as claimed herein.

A system, method and computer program product are provided to digitally process data in support of a medical diagnosis. More specifically, the embodiments relate to interpreting a series of data, or in one embodiment a plurality of images, acquired over time and providing a diagnosis or recommendation based on the interpretation. The embodiments relate to employing machine learning into the interpretation process and to automate interpretation of data in order to provide accurate interpretation output.

Data may be, but is not limited to, data acquired from one or more sensors and images. Medical sensor data may be acquired from, but is not limited to, an EEG. Similarly, medical image data may be acquired from, but is not limited to, one or more ultrasound images, an x-ray, one or more Magnetic Resonance Imaging (MRI) images, a Positron emission tomography (PET) Scan, a Single-photon emission computed tomography (SPECT) scan, an Optical coherence tomography (OCT) scan, one or more elastography images, one or more tactile images, one or more photoacoustic images, one or more thermographic images, an echocardiogram, one or more funduscopic images, a renal scan, and one or more functional near-infrared spectroscopic images.

Figure 1:
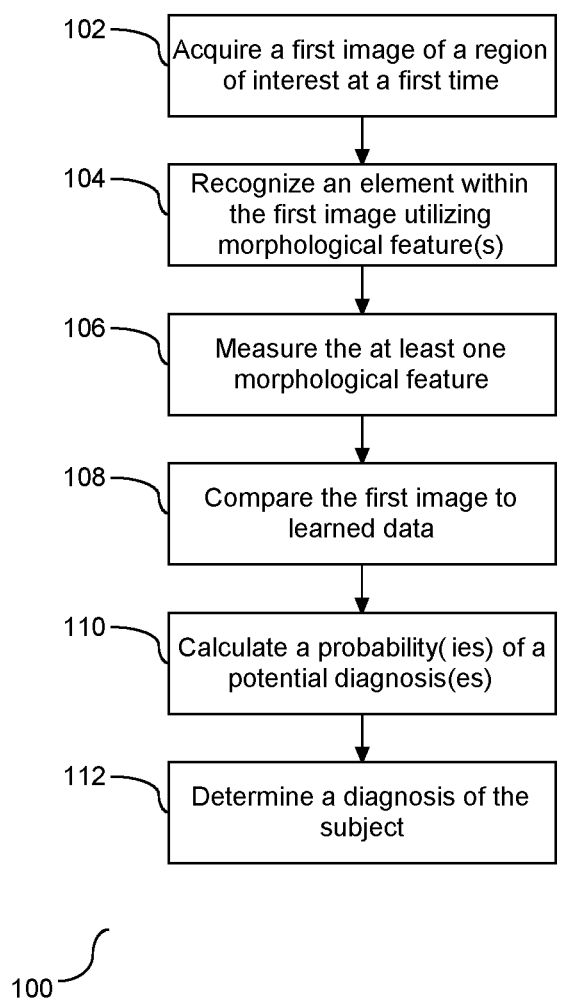
FIG. 1 depicts a flow chart illustrating an embodiment of interpreting an image based on learned data.

Referring to FIG. 1, a flow chart (100) is provided illustrating an embodiment of interpreting one or more images or medical related images based on machine learning. As shown, an image is acquired from a subject based on a predetermined region of interest at a first point-in-time (102). The region of interest is selected based on at least one predetermined element which relates to a probable indicator for a diagnosis. In one embodiment, the element will be tracked over time in order to determine changes and indicators of a condition in order to provide an accurate diagnosis. The element may be, but is not limited to, a dominant follicle, recessive follicle, vasculature, chamber size, fat, water, retina, lens, brain, muscle, tendon, ligament, or in one embodiment any other element that may be imaged within the subject. For example, if a diagnosis of an optimal time for insemination is desired, the region of interest would be the gland(s) and the tracked element would be a dominant follicle wherein the tracking will provide an indication of the proper time for insemination. Accordingly, a first image of a selected or designated element is acquired in order to acquire data for a diagnosis.

All images are subject to interpretation. Medical images are a class of images associated with interpreting a possible medical condition. As such, the interpretation may be considered of greater importance than that of a non-medical image. The image interpretation shown herein includes recognition of the selected or designated element within the image utilizing at least one morphological feature of the element (104). The morphological feature of the element may be, but is not limited to edge, size, shape, length, width, angle, tortuosity, and, color. The recognition utilizes learned data which contains other images associated with a similar region of interest of at least one previous subject, and in one embodiment at least one data file retained in data storage. In one embodiment, the image(s) contained in the data storage that are utilized for the recognition at step (104) contain one or more similar element(s) with at least one morphological feature for comparison. Additionally, the data file(s) employed or selected for the comparison may contain, but not limited to, an element definition (i.e. instruction on how to identify the element), morphological feature definition (i.e. instruction on how to identify the morphological feature), a template set for image recognition, a diagnosis of a subject and subject data. The subject data may be, but is not limited to, age, weight, blood pressure, glucose level, location, nationality, bodily configuration, medical history, or other data associated with the subject. The morphological features of the element may be recognized by, but is not limited to, a comparison to one or more stored image(s), morphological operators, edge detection, use of a template set, and/or use of instructions. Based on the morphological feature(s), the element that is the subject of the evaluation may be recognized and the morphological feature(s) of the element may be tracked. Accordingly, the data storage provides a resource for learned data for use in recognition of elements in order to increase the accuracy of the recognition and evaluation.

In order to provide an accurate recognition of a morphological feature, the data storage may be filtered to limit images and data files with similar subject data. For example, in one embodiment, data of the current subject may be used to eliminate at least one subject with dissimilar subject data. In one embodiment, the subject data may be used to assign a weight to each image of a subject in the data storage used for comparison. Accordingly, subject data may be used for filtering the data storage for comparison.

Following the recognition at step (104), the morphological feature(s) of the element is measured (106). Based on the recognition of the element and measurement of the morphological feature(s), the first image is compared to learned data, e.g. a previous image of a previous subject in the data storage (108). The comparison includes determining one or more similarities and/or differences between the morphological feature(s) of the current subject versus the morphological feature(s) of the previous subject(s), including similarity(ies) and/or difference(s) between measurement(s). Accordingly, the image of the current subject is compared to learned image data in order to determine similarities and differences.

Following the comparison at step (108), a potential diagnosis(es) is determined based on the comparison, and a probability(ies) of the potential diagnosis(es) is calculated based on the degree of similarity between the first image of the current subject and the image of a compared previous subject having the potential diagnosis (110). The probability is based on the degree of similarity between the morphological feature(s) of an element(s) within the first image and the morphological feature(s) of at least one image associated with the potential diagnosis. In one embodiment, the subject data of the current subject is utilized to increase or decrease the probability of a potential diagnosis. In one embodiment, the subject data of the current subject is utilized to filter the data storage before determining potential diagnosis(es). Accordingly, probabilities of potential diagnosis are assessed as part of the image and associated feature comparison.

After the calculation of the probability(ies) at step (110), a diagnosis of the current subject is determined (112). More specifically, the diagnosis is determined based on at least one potential diagnosis and the calculated probability of the potential diagnosis(es). In one embodiment, the diagnosis of the subject is based on the potential diagnosis with the highest probability. In one embodiment, the diagnosis of the subject is an aggregate of at least two diagnoses from at least two potential diagnoses and selection of the aggregate diagnosis. Accordingly, the diagnosis is determined by using learned data as a basis for comparison and probability assessment.

Figure 2:
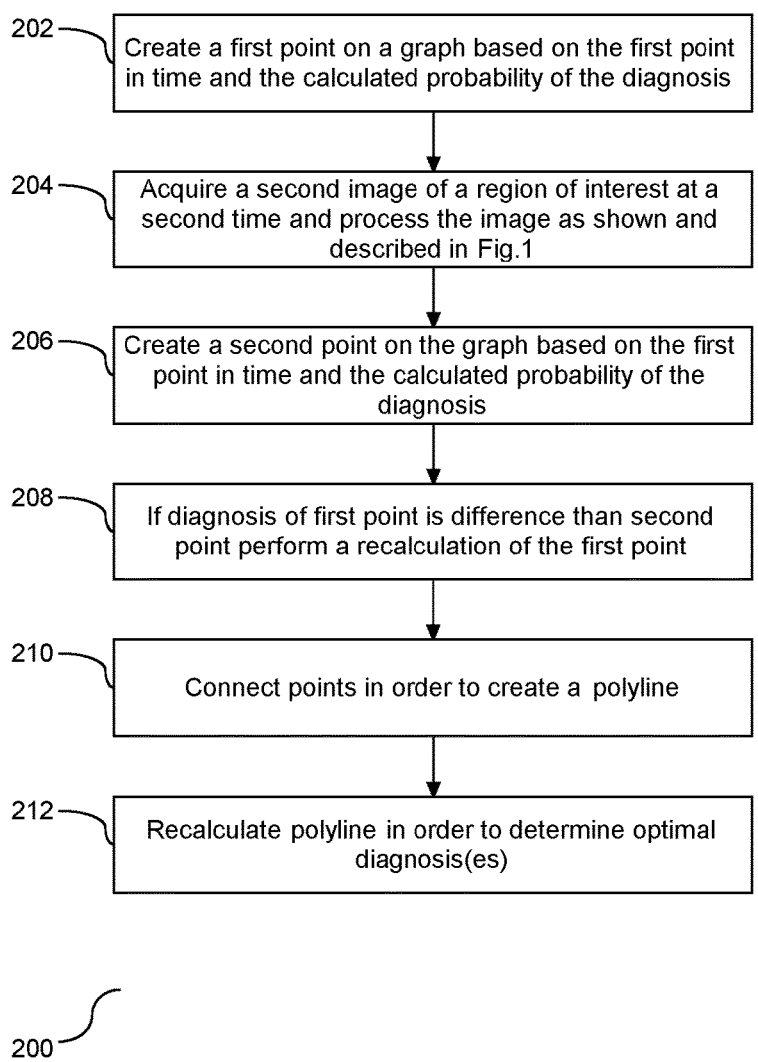
FIG. 2 depicts a flow chart illustrating an embodiment of diagnosing a subject utilizing multiple images acquired at different points in time.

Referring to FIG. 2, a flow chart (200) is provided illustrating an embodiment of diagnosing a subject utilizing multiple images acquired at different points in time and creating a graph for performing a time series analysis of the data. As shown in FIG. 1, a diagnosis is determined. A first point on a graph is created based on the calculated probability of the diagnosis (202). The point at step (202) corresponds to the first point-in-time (X-dimension) that the first image was acquired and the calculated probability of the diagnosis of the subject (Y-dimension). Accordingly, the graph entry created at step (202) serves as a basis to track the probability of a diagnosis of the subject over time.

A second image is acquired from the subject at a second point-in-time based on the pre-determined region of interest of the first image and process as shown and describe in FIG. 1, (204). In one embodiment, during recognition of the element in the second image a comparison to the first image is performed. In one embodiment, the image processing shown and described at step (204) includes a diagnosis pertaining to the second image. Accordingly, in addition to the first image and first diagnosis, a second diagnosis is determined based on the second image.

In response to the determination of the second diagnosis, a second point on the graph is created (206). The second point corresponds to the second point-in-time that the second image was acquired and the probability of the diagnosis of the subject. Additionally, if the diagnosis for the second point is different than the diagnosis for the first point then a re-calculation of the first point will be performed wherein the re-calculation is based on the diagnosis for the second point (208). Thus, the calculated probability for each point is based on the same diagnosis(es).

After creation of the second point, a line is created connecting the first point to the second point, thus creating a polyline based on data acquired from the subject (210). The polyline of the subject provides time dependent probability data based on a diagnosis of the subject and images taken of the subject over time. As described above, the points on the polyline are calculated based on the same diagnosis(es). The polyline can be re-calculated based on a different diagnosis. In one embodiment, the re-calculation of the polyline can be performed iteratively for different diagnoses until an optimal diagnosis is determined (212). The optimal diagnosis may be determined based on comparing different iterations of the polyline based on one or more parameters of the polyline. The one or more parameters may be, but is not limited to, probability value(s) of one or more points, an area under or above the polyline, slope(s), curvature, length(s), starting point, ending point, horizontal relation, vertical relation, standard deviation of two or more points, average of two or more points, median of three or more points, and mode of three or more points. In one embodiment, the optimal diagnosis is based on the one or more parameters and one or more respective threshold values. The quantity of iteration, images, or points should not be considered limiting. In one embodiment, the quantity may be based on a predetermined value. Further, a polyline may be recalculated based on learned data acquired after the polyline was created. Accordingly, the polyline is used to determine the probability of a diagnosis based on a time series analysis of images in order to find an optimal diagnosis for the subject.

Figure 3:
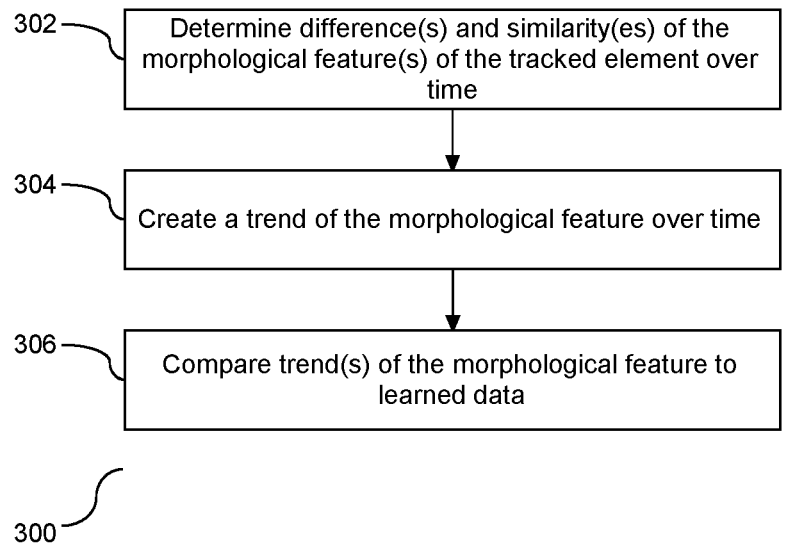
FIG. 3 depicts a flow chart illustrating a determination of trend(s) of morphological feature(s) over time.

Measurement trends of the morphological feature(s) show one or more time based changes or similarities of the morphological feature. Referring to FIG. 3, a flow chart (300) is provided illustrating a determination of trend(s) of morphological feature(s) over time. As shown, a determination of difference(s) and similarity(ies) of the morphological feature(s) of the tracked element(s) over time is performed (302). The difference(s) and similarity(ies) of the morphological feature(s) are determined and used to create a trend of the morphological feature (304). The trend(s) of the morphological feature(s) is compared to learned data, e.g. a trend(s) of a morphological feature(s) of previous subjects in the data storage. The trend(s) provide another form of comparison to learned data in order to achieve a more accurate diagnosis of the subject. Accordingly, a trend is created and used to determine similar trend(s) of corresponding or similar diagnosis(es).

Figure 4:
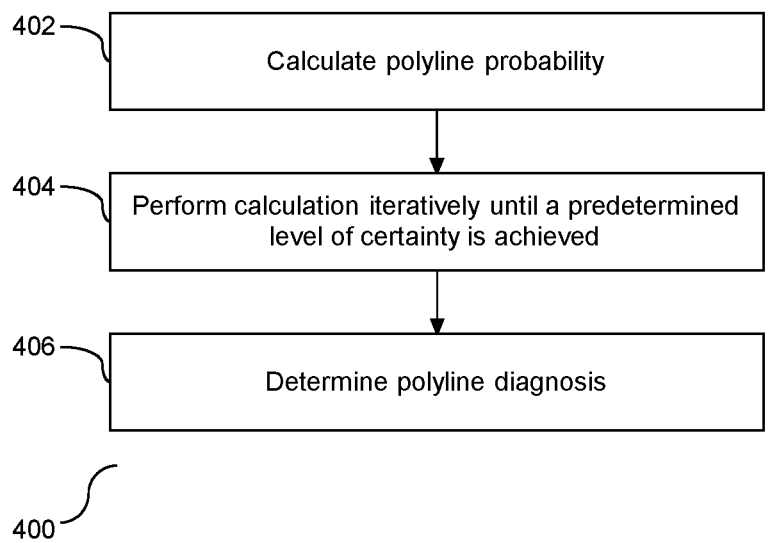
FIG. 4 depicts a flow chart illustrating a determination of a polyline diagnosis of a subject.

The polyline created in FIG. 2 may be subject to further analysis and re-calculation. Referring to FIG. 4, a flow chart (400) is provided illustrating a determination of a polyline diagnosis of a subject. As shown, a polyline probability is calculated, and in one embodiment re-calculated, using a probabilistic framework and risk analysis utilizing multiple dimensions in order to perform a comparison of the individual time points and the polyline as a whole to learned data (402). A higher polyline probability value implies that the polyline of the subject has a high similarity to the compared diagnosis. Conversely, a lower polyline probability implies that there are fewer similarities to the compared diagnosis. Accordingly, the polyline is used to determine the likelihood of a subject having a condition based on a comparison of data acquired from the subject over time to learned data.

In order to determine the polyline probability(ies) of potential polyline diagnosis(es), a weight is assigned to each morphological feature and in one embodiment each time point. The weight may be determined from learned data, and in one embodiment examining stored data. Calculating polyline probabilities includes substituting a range of values for each morphological feature measurement used to construct a point on the polyline. In one embodiment, the measurement of each morphological feature at each time point has the measured value substituted for a range of values depending on the measurement error. The calculation is performed iteratively, each iteration using a different set of random values as inputs to the probability functions of each point on the polyline until a predetermined level of certainty is achieved (404). The calculation may include but is not limited to, Monte Carlo simulations, Wavelet analysis, or Markov chains. Accordingly, a polyline probability is calculated in order to analyze the time series of acquired images.

A polyline diagnosis of the subject is determined utilizing the list of possible polyline diagnosis(es) (406). In one embodiment, the polyline diagnosis is the potential diagnosis with the highest probability value (406). In one embodiment, the polyline line diagnosis is used when selecting a treatment to perform on a subject, and following the selection the treatment is performed. In one embodiment, the polyline is used by a physician or medical professional examining the subject as a visual aid in order to make a determination of a diagnosis and a proper course of treatment to perform on the subject. Accordingly, a polyline diagnosis allows a determination of a diagnosis based on a probabilistic framework and risk analysis utilizing multiple dimensions of data.

In one embodiment, an aggregated case is created and stored for comparison to subjects. An aggregated case is based on the data and images acquired from a plurality of subjects. All subjects with a similar diagnosis may be aggregated into a single aggregated case. The aggregated case provides a method to search stored data, compare data, process data, and calculate a probability(ies). The aggregated case enables a determination of an accurate diagnosis of the subject since the aggregated case is based on multiple subjects with similar diagnoses instead of a single subject. Additionally, the aggregated case may contain aggregated images. The aggregated images are images created based on the images acquired from each subject that is a member of the aggregated case. Each morphological feature of each element is created based on the similarities and differences between each subject of the aggregated case. In one embodiment, the subjects used to create an aggregated case have similar subject data. Further, the aggregated case may contain an aggregated template for image analysis. Accordingly, an aggregated case is created to summarize learned data for an accurate diagnosis and more efficient search of the stored data.

As described herein, ultrasound images may be used for reproductive studies to diagnose an optimal time for insemination of a subject. In order to determine the optimal time, a complete understanding of the gland's follicle dynamics is crucial. One skilled in the art would recognize that the dominant follicle(s) which have the potential to produce and discharge responsive to a function of the gland must be identified. Not all dominant follicles produce and discharge responsive to a function of the gland, and not all dominant follicles are of sufficient quality to result in pregnancy. As such, the dominate follicles must be characterized. The characterization can occur through a comparison between dominant follicles resulting in pregnancy, and those less dominant follicles that did not result in pregnancy. Accordingly, comparison of dominant follicles is crucial in order to provide an accurate diagnosis of an optimal time for insemination.

It is understood that during image processing, follicles are difficult to characterize even though, basic image processing steps are required for their recognition (i.e. preprocessing, segmentation, feature extraction and classification). Features such as blood vessels, lymphatic glands, and nerve fibers present in ultrasound images cause issues with recognizing particular element(s). Further, speckle noise inherent to ultrasound imaging inhibits element recognition. A cellular neural network (CNN) coupled with learned data is employed to improve the follicle recognition and mitigate the inherent issues associated with ultrasound imaging and processing.

A CNN constitutes a class of recurrent and locally coupled arrays of simple processing elements (cells). In a CNN, information is directly exchanged between neighboring cells allowing for increased learning of representations of key elements and their corresponding morphological features. The connectivity among the cells is determined using a set of parameters denoted as a template set, which can be initialized based on the template set stored in data storage. The template set can be dynamically updated based on newly acquired data. The template set provides a method for the CNN to learn thereby providing more efficient recognition of elements and an accurate diagnosis(es). The CNN architecture provided for follicle detection utilizes two sequentially connected CNNs wherein each image pixel links to a CNN cell. The CNN architecture utilizes the learned data during element recognition, which provides improved preprocessing, segmentation and recognition within the acquired image. Accordingly, a deep CNN architecture that preserves the translation in sequential frames, learns from these translations and renders an improved representation is provided.

Figure 5:
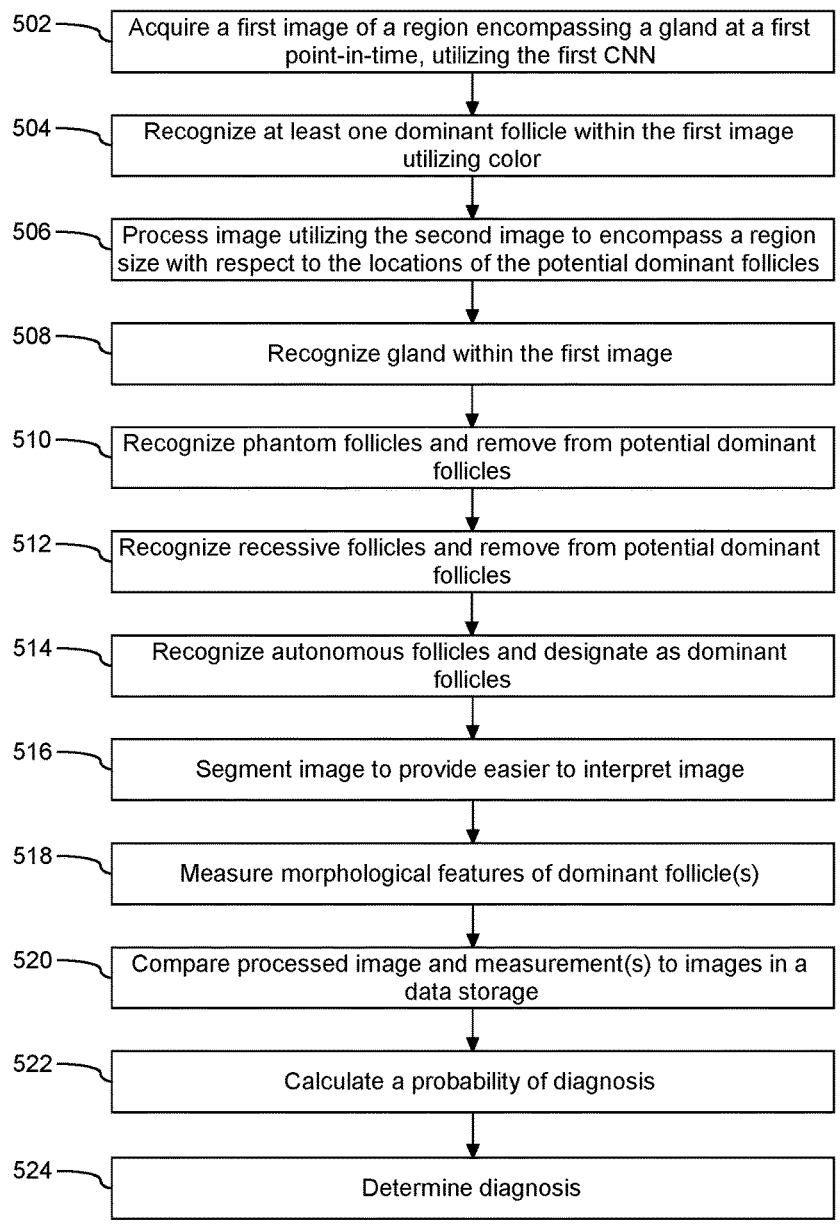
FIG. 5 depicts a flow cart illustrating an embodiment for determining a diagnosis of an optimal time for insemination of a subject.

Referring to FIG. 5, a flow chart (500) is provided illustrating an embodiment of determining a diagnosis of an optimal time for insemination based on an image of a subject. As shown, a first image of a region encompassing at least one gland of a subject at a first point-in-time is acquired, utilizing a first CNN (502). The gland contains follicles which must be monitored and tracked in order to determine the optimal time for insemination. Following acquisition of the image, one or more potential dominant follicle(s) are recognized within the first image utilizing a morphological feature based on the template set (504). In an ultrasound, the recognition utilizes the morphological feature of color including determining the darkest object(s) in the image. In one embodiment, the recognition parameters (i.e. how to determine a threshold for "darkest") are contained in the template set. In one embodiment, the recognition parameters are stored as instruction(s) in data storage and are referenced in order to determine elements in the image. In one embodiment, the template is updated based on the recognition of the current image. Accordingly, the darkest object(s) in the image are recognized as potential dominant follicle(s).

The image created following step (504) is further processed utilizing a second CNN (506). The processing in step (506) includes changing the region of interest to encompass only a region sized with respect to the locations of the potential dominant follicles found in step (504). In one embodiment, the changing of the region is performed based on parameters in a template set. Accordingly, the region of interest is changed to encompass only those elements found to be potential dominant follicle(s).

The processed image output at step (506) and the original first image are exploited by the two sequentially connected CNNs to recognize a gland, with the exploitation utilizing morphological features of the gland (508). In one embodiment, the gland is recognized based on parameters in the template set. Phantom follicles are recognized and eliminated from the potential dominant follicle(s) (510). Phantom follicles are not within the boundary of the gland, thus the recognition of phantom follicles utilizes the morphological feature of location. Any follicle having a location outside the boundary of the gland is removed from potential dominant follicles. Accordingly, as shown herein the phantom follicles are removed from the potential dominant follicle(s).

The processed image output from step (510) is used to recognize recessive follicle(s) and remove the recognized recessive follicle(s) from the potential dominant follicle(s) (512). The recognition is performed only on the region of the image that contains the potential dominant follicles. The recognition utilizes brightness of the image and lowers the bias of the image to determine recognized follicles over a brightness threshold and determine the recognized follicles over the threshold are recessive follicle(s). The lowering of the bias limits the intensity gradient shown in the image. In one embodiment, the threshold for brightness and bias lowering parameters are adjustable. Similarly, in one embodiment, the threshold for brightness and bias lowering parameters are stored in the template set. Lowering the bias enables the sequentially connected CNNs to efficiently and accurately segment the image. Accordingly, as shown, recessive follicles are determined, segmented, and removed from the potential dominant follicles.

Following step (512) autonomous follicles are recognized from the remaining potential dominate follicle(s) and designated as actual dominate follicle(s) (514). Dominant follicles do not connect two follicles. Therefore, determining autonomous follicles provides the actual dominate follicle(s). The recognition utilizes boundaries of the potential dominant follicles to determine if any potential dominant follicle intersects with another potential dominant follicle. Any potential dominant follicle which intersects two or more potential dominant follicles is removed from designation as a potential dominant follicle(s). Following any removals, the remaining potential dominant follicle(s) are actual dominant follicle(s). In one embodiment, the procedure for determining the actual dominant follicle is stored in the template set. In one embodiment, the dominant follicles are segmented in the image and used to create an interpretable image (516). The interpretable image may be used by a physician, or medical professional, examining the subject. Accordingly, the segmentation in the image functions as a basis to interpret and can be used to provide a diagnosis(es).

Following the recognition of the dominant follicle(s), the morphological features of the dominant follicles are measured (518). Such measured features include, but are not limited to, edge intensity, shape, size, and color. In one embodiment, gray-scale features and gray-scale gradient features are achieved through a wavelet analysis. The processed image and measured morphological features are compared to one or more previously storage images and associated measurements (520). The comparison includes determining similarities and differences between the dominant follicles of the current subject versus the dominant follicles of a previous subject(s) including similarities and differences between measurement(s). Accordingly, the recognized dominant follicles are compared to the learned data.

Based on the comparison, a probability(ies) of a diagnosis(es) (i.e. optimal time to inseminate the subject) is calculated based on the degree of similarity between the dominant follicles of the current subject and the dominant follicles of a compared previous subject (522). A potential time for insemination is determined from the stored data based on the comparison, and a probability of the time for insemination calculated based on a comparison of the dominant follicles. The probability is based on the degree of similarity between the dominant follicle(s) of the current subject and the dominant follicle(s) of at least one image associated with the potential diagnosis. After the calculation of the probability(ies), the diagnosis of the optimal time for insemination is determined (524). The diagnosis of the subject is determined based on at least one potential diagnosis. In one embodiment, the diagnosis of the subject is determined based on the potential diagnosis with the highest calculated probability. In one embodiment, the determined diagnosis and calculated probability are displayed on or near the interpretable image and key morphological features (determined from learned data) in the interpretable image used in making the diagnosis are highlighted or otherwise identified. Accordingly, the optimal time for insemination is determined based on comparison to learned data.

Figure 6:
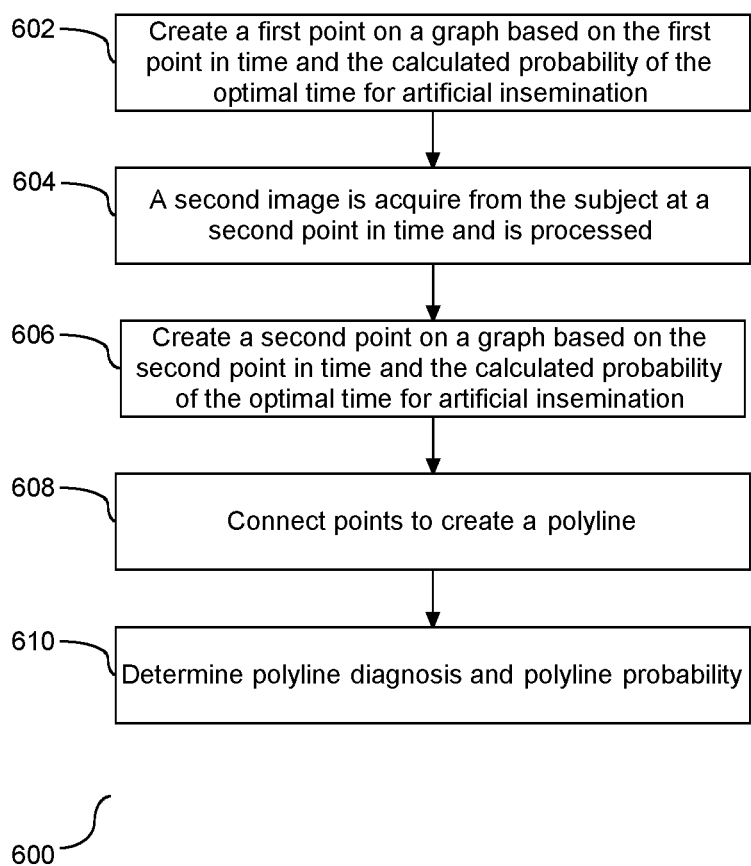
FIG. 6 depicts a flow chart illustrating an embodiment for determining an optimal time for insemination based on a time series analysis of a subject.

Referring to FIG. 6 a flow chart (600) is provided illustrating an embodiment for determining an optimal time for insemination based on a time series analysis of the subject. As shown, a first point on a graph is created based on the first point-in-time that the first image was acquired and the calculated probability of the optimal time for insemination (602). Accordingly, the graph is used to track the probability of the optimal time for insemination over time.

Following initiation of the graph at step (602), data is acquired from the subject over time. For instance, a second image is acquired from the subject at a second point-in-time based on the predetermined region of interest of the first image utilizing the steps as shown and described in FIG. 5, (604). Following the acquisition, processing, segmentation and measurement of the second image a second point on the graph is created (606). The second point corresponds to the second point-in-time that the second image was acquired and the probability of the optimal time for insemination. All points on the graph correspond to the same diagnosis(es). Thus, if the diagnosis for the second point is different than the diagnosis for the first point then a re-calculation of the first point will be performed based on the diagnosis of the second point. Accordingly, all points on the graph are calculated based on the same diagnosis(es).

A line is created connecting the first point to the second point creating a polyline (608). Similar to FIG. 2 step (212), in one embodiment, the re-calculation of the polyline can be performed iteratively for different diagnoses until an optimal diagnosis is determined. The quantity of images acquired and points created on a graph should not be considered limiting. A polyline diagnosis of the optimal time for insemination is determined based on a change in the dominate follicles as shown and described in FIG. 4, (610). In one embodiment, a diagnosis image may be created which includes, the polyline, the polyline diagnosis, the calculated polyline probability, and the interpretable image. In one embodiment, the diagnosis image is used by a physician, or other medical professional, examining the subject as a visual aid in order to make a determination of a diagnosis and a proper course of treatment to perform on the subject. Accordingly, the polyline is used to determine the optimal time for insemination and the probability of the optimal time for insemination.

In one embodiment, polycystic gland syndrome (PCGS) may be detected. PCGS is a common hormonal disorder that causes enlarged glands containing numerous cysts located across the outer edge of each gland. PCGS detection acquires a series of pelvic ultrasounds lasting over the entire menstrual cycle of a subject in order to monitor follicular growth and capture the gland's response when subjected to follicle tracking treatments. Various morphological features can be tracked in order to diagnosis PCGS such as, but not limited to, shape, antral edge quality, size and echogenicity. Further, the current embodiments reduce the time overheads require by manual studying of ultrasound images thereby providing efficiency to the study and diagnosis process.

Figure 7:
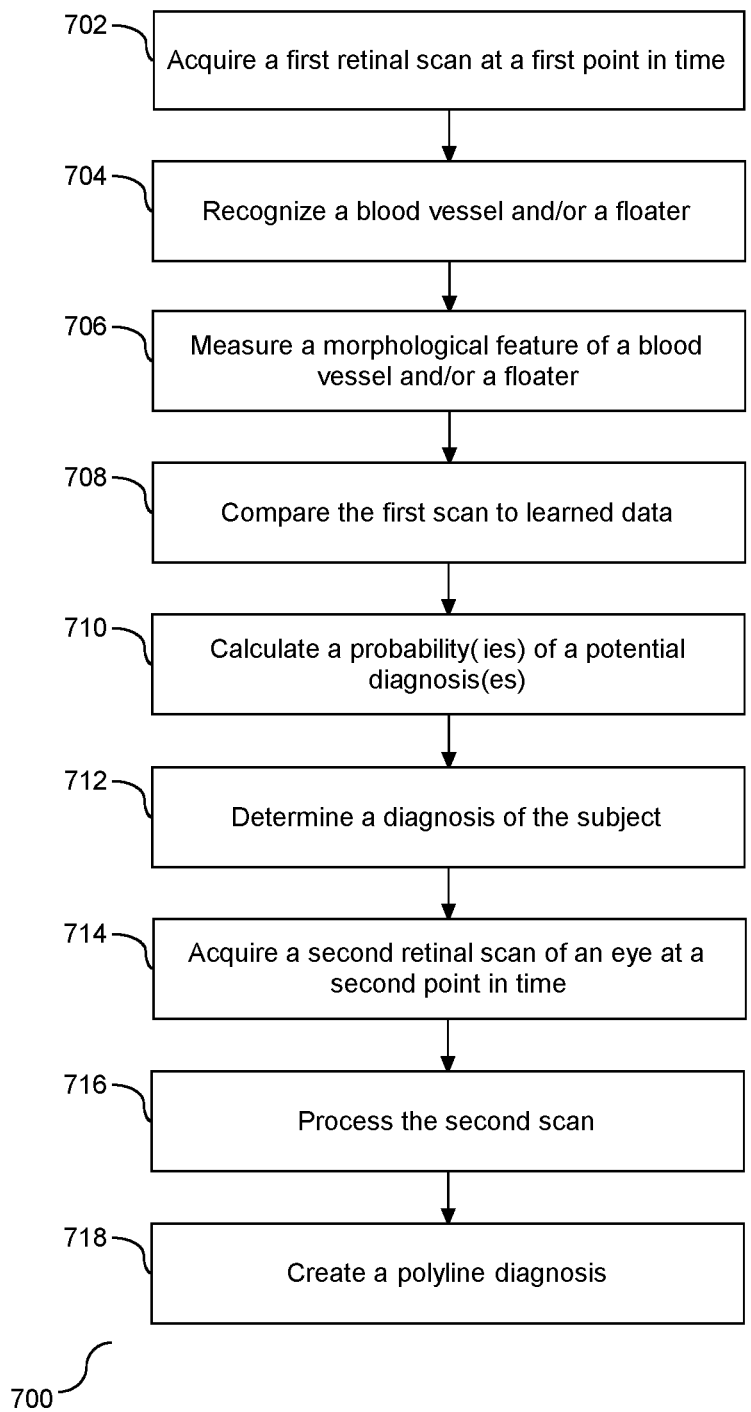
FIG. 7 depicts a flow chart illustrating an embodiment for determining a diagnosis of diabetic retinopathy based on a retinal scan.

In one embodiment, the evaluation and diagnosis prediction shown and described above may be applied to detection of diabetic retinopathy. Diabetic retinopathy affects blood vessels in light-sensitive tissues, e.g. the retina, which lines the back of the eye. Referring to FIG. 7, a flow chart (700) is provided illustrating an embodiment of determining a diagnosis of diabetic retinopathy based on a retinal scan. Diabetic retinopathy detection acquires a retinal scan, e.g. Optical Coherence Tomography (OCT) scan, of a subject's eye at a first point in time (702). The retinal scan is processed in order to recognize blood vessel(s) and/or floater(s), e.g. vitreous jelly that may start to form in the eye indicating damage (704). The recognition utilizes morphological features of the blood vessel and floater such as, but not limited to, diameter, length, branching angle, and tortuosity. Additionally, the recognition utilizes learned data which contains other retinal scans associated with an eye of at least one previous subject. Accordingly, learned data is utilized in order to increase the accuracy of recognition of blood vessels and floaters for determining a diagnosis related to diabetic retinopathy.

The morphological feature(s) of the blood vessel and/or floater is measured (706). Based on the recognition of the blood vessel and/or floater and measurement of their respective morphological feature, the first scan is compared to learned data, e.g. a previous retinal scan of a previous subject in data storage (708). Following the comparison at step (708), a potential diagnosis(es) is determined based on the comparison, and a probability(ies) of the potential diagnosis(es) is calculated based on the degree of similarity between the first retinal scan of the current subject and the compared retinal scan of a previous subject having the potential diagnosis (710). After the calculation of the probability at step (710), a diagnosis of the current subject is determined (712). In one embodiment, an interpretable image may be created from the retinal scan, determined probability, determined diagnosis, and/or morphological feature(s). Accordingly, the diagnosis is determined by using learned data as a basis for comparison and probability assessment.

In one embodiment, at least one additional retinal scan of the subject is acquired at a second point in time to determine any changes in the morphological feature(s) from the first point in time to the second point in time (714). The scan(s) is then processed (716) as shown and described in steps (704)-(712). Change in the morphological feature(s) over time can indicate change(s) in the blood vessel(s), swelling and leaking, and floater(s) which are indicative of diabetic retinopathy. Based upon the first OCT scan and the second OCT scan a polyline diagnosis is created (718), as shown and described in FIGS. 2-4. The quantity of scans and points in time the scans are acquired should not be considered limiting. Accordingly, the processes shown and described in FIGS. 1-4 may be expanded to the field of study of diabetic retinopathy by monitoring floaters and blood vessels in the eye through associated retinal scans.

Figure 8:
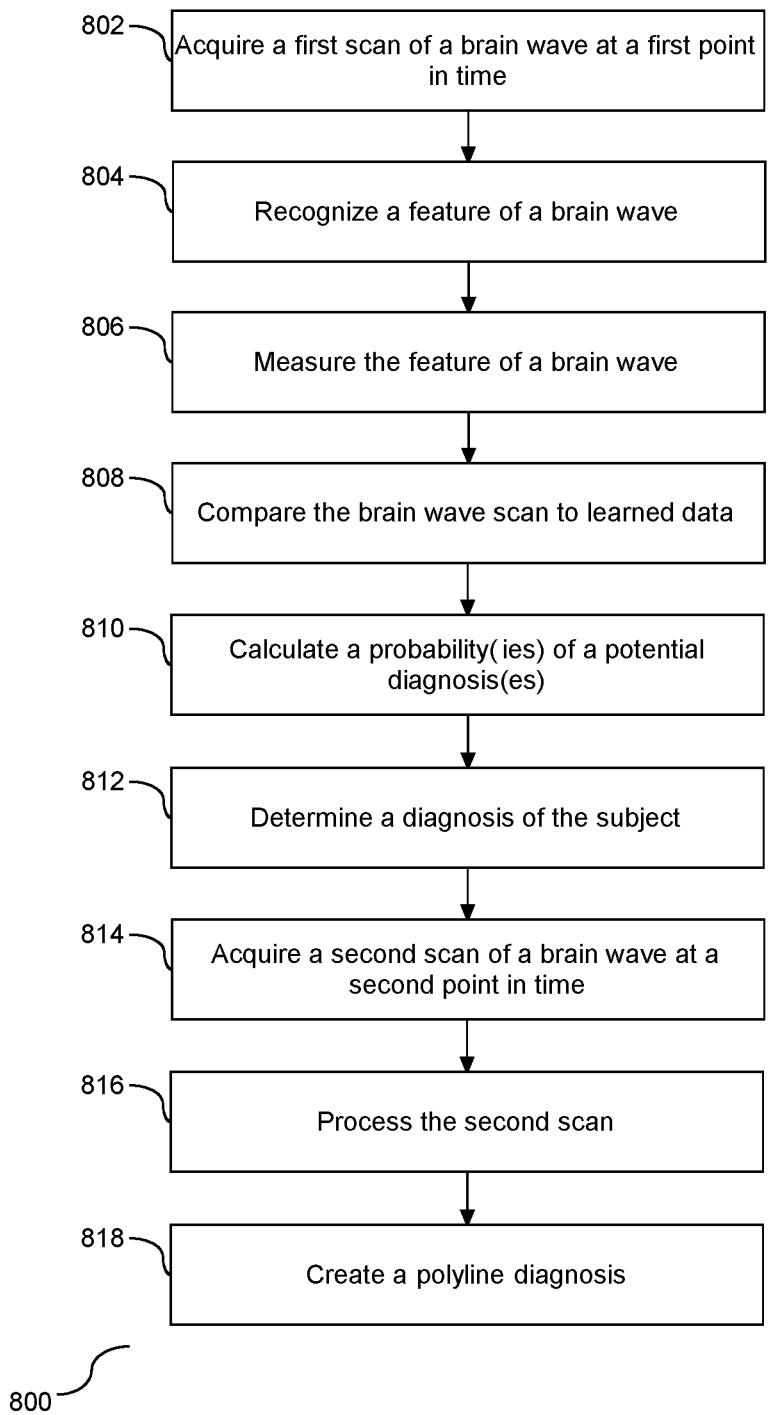
FIG. 8 depicts a flow chart illustrating an embodiment for determining a diagnosis of a seizure based on a brain wave scan.

In another embodiment, the process of image evaluation and diagnosis may be applied to the detection of epileptic seizures. Referring to FIG. 8, a flow chart (800) is provided illustrating an embodiment of determining a diagnosis of a seizure based on a brain wave scan. Seizure detection acquires a scan of a subject's brainwave, hereinafter "brain wave scan", at a first point in time (802). For example, an EEG or an electrocorticogram (ECoG) may be used to acquire a brain wave scan. The EEG and ECoG provide data about the subject's brain waves, i.e voltage fluctuations, usually viewed as a graph. Features of the brain waves in the graph are recognized (804) and measured (806). The recognition utilizes learned data which contains other scan(s) associated with brain wave(s) of at least one previous subject. Accordingly, learned data is utilized in order to increase the accuracy of recognition of brain wave feature(s) for determining a diagnosis related to seizures.

The brain wave feature(s) is compared to a data storage of learn data containing other brain wave scan(s) of a previous subject(s) and brain wave feature(s) indicative of a seizure (808). Following the comparison at step (808), a potential diagnosis(es) is determined based on the comparison, and a probability(ies) of the potential diagnosis(es) is calculated based on the degree of similarity between the first brain wave scan of the current subject and a compared brain wave scan of a previous subject having the potential diagnosis (810). After the calculation of the probability at step (810), a diagnosis of the current subject is determined (812). In one embodiment, an interpretable image may be created from the brain wave scan (e.g EEG), determined probability, determined diagnosis, and/or morphological feature(s) and presented on a display device. Accordingly, the diagnosis is determined by using learned data as a basis for comparison and probability assessment.

In one embodiment, an additional brain wave scan of the subject is acquired at a second point in time to determine any changes in the morphological feature(s) from the first point in time to the second point in time (814). The brain wave scan(s) is then processed (816) as shown and described in steps (804)-(812). Based upon the first brain wave scan and the second brain wave scan a polyline diagnosis is created (818) as shown and described in FIGS. 2-4. The quantity of brain wave scans and points in time the brain wave scans are acquired should not be considered limiting. In one embodiment, in order to determine a polyline diagnosis, a time series analysis of the brain wave scans is calculated utilizing a Markov Chain to compute a multiple dimension joint probability of a potential diagnosis(es) (i.e. time of next seizure). During the calculation, a weight is assigned to every characteristic in the EEG signal that is deterministic of a seizure. After the calculation, the time of subject's next seizure is determined, or in one embodiment, projected, based on the potential time of the next seizure with the highest probability. In one embodiment, CT scans and MRIs may be acquired and monitored over time to determine abnormalities in the brain for predicting seizures. Accordingly, the processes shown and described in FIGS. 1-4 may be expanded to the field of study of seizures by monitoring brain waves through associated brain wave scans, such as an EEG.

Aspects of interpreting a series of images acquired from a subject over time and providing a diagnosis based on the interpretation provided in FIGS. 1-8, employ one or more functional tools to support use of a prediction pertaining to a medical condition. Aspects of the functional tool, e.g. Image Diagnostic Tool or Scan Diagnostic Tool, and its associated functionality may be embodied in a computer system/server in a single location, or in one embodiment, may be configured in a cloud based system sharing computing resources. With references to FIG. 9, a block diagram (900) is provided illustrating an example of a computer system/server (902), hereinafter referred to as a host (902) in communication with a cloud based support system, to implement the processes described above with respect to FIGS. 1-8. Host (902) is operational with numerous other general purpose or special purpose computing system environments or configurations. Examples of well-known computing systems, environments, and/or configurations that may be suitable for use with host (902) include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and file systems (e.g., distributed storage environments and distributed cloud computing environments) that include any of the above systems, devices, and their equivalents.

Host (902) may be described in the general context of computer system-executable instructions, such as program modules, being executed by a computer system. Generally, program modules may include routines, programs, objects, components, logic, data structures, and so on that perform particular tasks or implement particular abstract data types. Host (902) may be practiced in distributed cloud computing environments where tasks are performed by remote processing devices that are linked through a communications network. In a distributed cloud computing environment, program modules may be located in both local and remote computer system storage media including memory storage devices.

Figure 9:
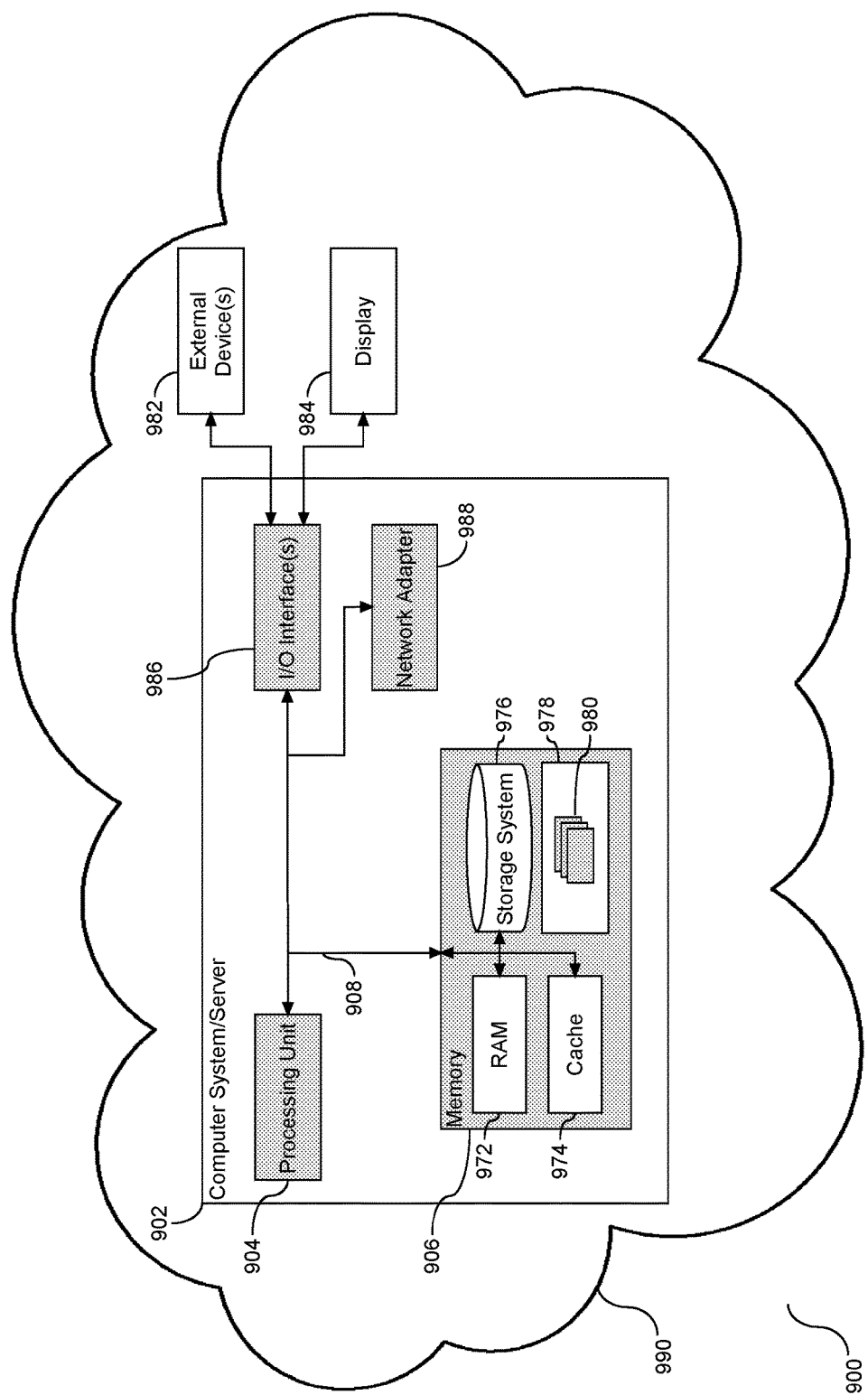
FIG. 9 is a block diagram illustrating an example of a computer system/server of a cloud based support system, to implement the process described above with respect to FIGS. 1-8.

As shown in FIG. 9, host (902) is shown in the form of a general-purpose computing device. The components of host (902) may include, but are not limited to, one or more processors or processing units (904), a system memory (906), and a bus (908) that couples various system components including system memory (906) to processor (904). Bus (908) represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Host (902) typically includes a variety of computer system readable media. Such media may be any available media that is accessible by host (902) and it includes both volatile and non-volatile media, removable and non-removable media.

Memory (906) can include computer system readable media in the form of volatile memory, such as random access memory (RAM) (972) and/or cache memory (974). By way of example only, storage system (976) can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus (908) by one or more data media interfaces.

Program/utility (978), having a set (at least one) of program modules (980), may be stored in memory (906) by way of example, and not limitation, as well as an operating system, one or more application programs, other program modules, and program data. Each of the operating systems, one or more application programs, other program modules, and program data or some combination thereof, may include an implementation of a networking environment. Program modules (980) generally carry out the functions and/or methodologies of embodiments to store and analyze data. For example, the set of program modules (980) may include the modules configured as an Image Diagnostic Tool in order to interpret a series of images acquired from a subject over time and provide a diagnosis based on the interpretation as shown and described in FIGS. 1-8.

Host (902) may also communicate with one or more external devices (982), such as a keyboard, a pointing device, etc.; a display (984); one or more devices that enable a user to interact with host (902); and/or any devices (e.g., network card, modem, etc.) that enable host (902) to communicate with one or more other computing devices. Such communication can occur via Input/Output (I/O) interface(s) (986). Still yet, host (902) can communicate with one or more networks such as a local area network (LAN), a general wide area network (WAN), and/or a public network (e.g., the Internet) via network adapter (988). As depicted, network adapter (988) communicates with the other components of host (902) via bus (908). In one embodiment, a plurality of nodes of a distributed file system (not shown) is in communication with the host (902) via the I/O interface (986) or via the network adapter (988). It should be understood that although not shown, other hardware and/or software components could be used in conjunction with host (902). Examples, include, but are not limited to: microcode, device drivers, redundant processing units, external disk drive arrays, RAID systems, tape drives, and data archival storage systems, etc.

In this document, the terms "computer program medium," "computer usable medium," and "computer readable medium" are used to generally refer to media such as main memory (906), including RAM (972), cache (974), and storage system (976), such as a removable storage drive and a hard disk installed in a hard disk drive.

Computer programs (also called computer control logic) are stored in memory (906). Computer programs may also be received via a communication interface, such as network adapter (988). Such computer programs, when run, enable the computer system to perform the features of the present embodiments as discussed herein. In particular, the computer programs, when run, enable the processing unit (904) to perform the features of the computer system. Accordingly, such computer programs represent controllers of the computer system.

The present embodiments may be a system, a method, and/or a computer program product. The computer program product may include a computer readable storage medium (or media) having computer readable program instructions thereon for causing a processor to carry out aspects of the present embodiments.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present embodiments may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present embodiments.

In one embodiment, host (902) is a node (990) of a cloud computing environment. As is known in the art, cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models. Example of such characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Figure 10:
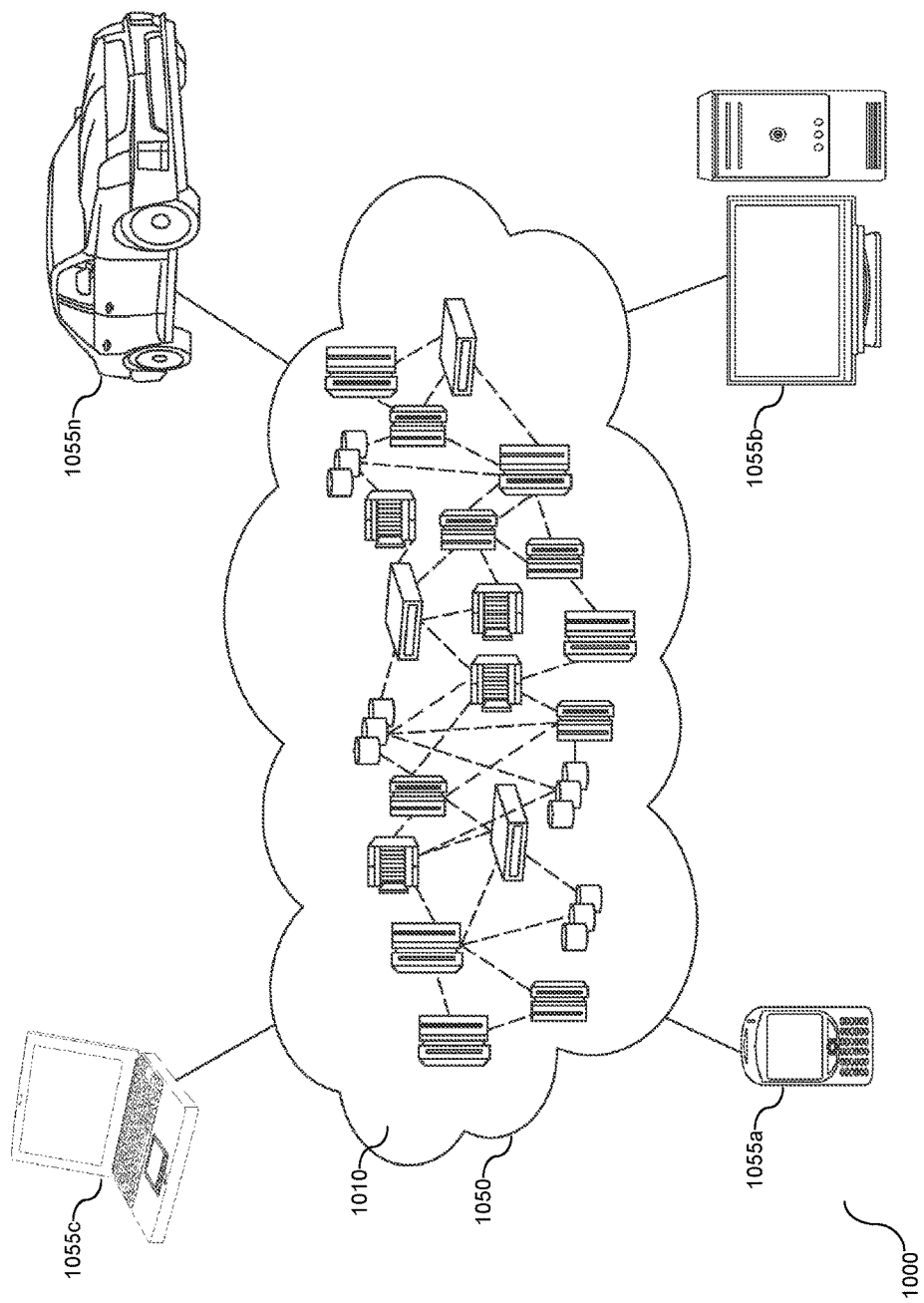
FIG. 10 depicts a block diagram illustrating a cloud computer environment.

Referring now to FIG. 10, an illustrative cloud computing network (1000). As shown, cloud computing network (1000) includes a cloud computing environment (1050) having one or more cloud computing nodes (1010) with which local computing devices used by cloud consumers may communicate. Examples of these local computing devices include, but are not limited to, personal digital assistant (PDA) or cellular telephone (1055A), desktop computer (1055B), laptop computer (1055C), and/or automobile computer system (1055N). Individual nodes within nodes (1010) may further communicate with one another. They may be grouped (not shown) physically or virtually, in one or more networks, such as Private, Community, Public, or Hybrid clouds as described hereinabove, or a combination thereof. This allows cloud computing environment (1000) to offer infrastructure, platforms and/or software as services for which a cloud consumer does not need to maintain resources on a local computing device. It is understood that the types of computing devices (1055A-N) shown in FIG. 10 are intended to be illustrative only and that the cloud computing environment (1050) can communicate with any type of computerized device over any type of network and/or network addressable connection (e.g., using a web browser).

Figure 11:
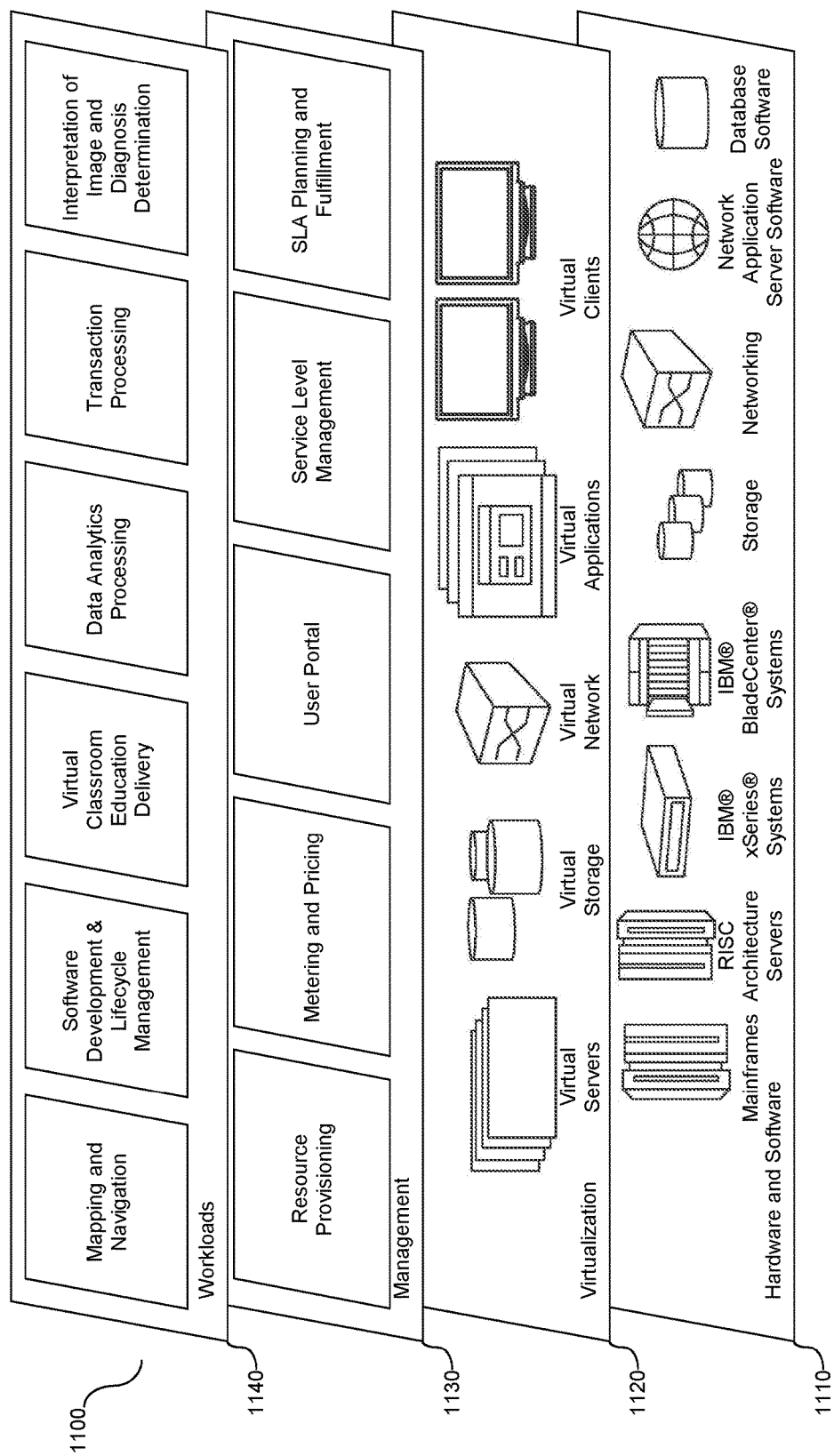
FIG. 11 depicts a block diagram illustrating a set of functional abstraction model layers provided by the cloud computing environment.

Referring now to FIG. 11, a set of functional abstraction layers provided by the cloud computing network of FIG. 9 is shown. It should be understood in advance that the components, layers, and functions shown in FIG. 11 are intended to be illustrative only, and the embodiments are not limited thereto. As depicted, the following layers and corresponding functions are provided: hardware and software layer (1110), virtualization layer (1120), management layer (1130), and workload layer (1140). The hardware and software layer (1110) includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer (1120) provides an abstraction layer from which the following examples of virtual entities may be provided: virtual servers; virtual storage; virtual networks, including virtual private networks; virtual applications and operating systems; and virtual clients.

In one example, management layer (1130) may provide the following functions: resource provisioning, metering and pricing, user portal, service level management, and SLA planning and fulfillment. Resource provisioning provides dynamic procurement of computing resources and other resources that are utilized to perform tasks within the cloud computing environment. Metering and pricing provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provides pre-arrangement for, and procurement of, cloud computing resources for which a future requirement is anticipated in accordance with an SLA.

Workloads layer (1140) provides examples of functionality for which the cloud computing environment may be utilized. Examples of workloads and functions which may be provided from this layer include, but are not limited to: mapping and navigation; software development and lifecycle management; virtual classroom education delivery; data analytics processing; transaction processing; and interpretation of images acquired from a subject over time and determination of a diagnosis based on the interpretation.

As will be appreciated by one skilled in the art, the aspects may be embodied as a system, method, or computer program product. Accordingly, the aspects may take the form of an entirely hardware embodiment, an entirely software embodiment (including firmware, resident software, micro-code, etc.), or an embodiment combining software and hardware aspects that may all generally be referred to herein as a "circuit," "module," or "system." Furthermore, the aspects described herein may take the form of a computer program product embodied in one or more computer readable medium(s) having computer readable program code embodied thereon.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

The embodiments are described above with reference to flow chart illustrations and/or block diagrams of methods, apparatus (systems), and computer program products. It will be understood that each block of the flow chart illustrations and/or block diagrams, and combinations of blocks in the flow chart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flow chart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flow chart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions, which execute on the computer or other programmable apparatus, provide processes for implementing the functions/acts specified in the flow chart and/or block diagram block or blocks.

The flow charts and block diagrams in the Figures illustrate the architecture, functionality, and operation of possible implementations of systems, methods, and computer program products according to various embodiments. In this regard, each block in the flow charts or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flow chart illustration(s), and combinations of blocks in the block diagrams and/or flow chart illustration(s), can be implemented by special purpose hardware-based systems that perform the specified functions or acts, or combinations of special purpose hardware and computer instructions.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The embodiments described herein may be implemented in a system, a method, and/or a computer program product. The computer program product may include a computer readable storage medium (or media) having computer readable program instructions thereon for causing a processor to carry out the embodiments described herein.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmissions, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

The embodiments are described herein with reference to flow chart illustrations and/or block diagrams of methods, apparatus (systems), and computer program products. It will be understood that each block of the flow chart illustrations and/or block diagrams, and combinations of blocks in the flow chart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flow chart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flow chart and/or block diagram block or blocks.

It will be appreciated that, although specific embodiments have been described herein for purposes of illustration, various modifications may be made without departing from the spirit and scope of the specific embodiments described herein. Accordingly, the scope of protection is limited only by the following claims and their equivalents.

Aspects of the present embodiments are described herein with reference to flowchart illustrations and/or block diagrams of methods, apparatus (systems), and computer program products according to embodiments. It will be understood that each block of the flowchart illustrations and/or block diagrams, and combinations of blocks in the flowchart illustrations and/or block diagrams, can be implemented by computer readable program instructions.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The corresponding structures, materials, acts, and equivalents of all means or step plus function elements in the claims below are intended to include any structure, material, or act for performing the function in combination with other claimed elements as specifically claimed. The description of the present embodiments has been presented for purposes of illustration and description, but is not intended to be exhaustive or limited to the embodiments in the form disclosed.

Indeed, executable code could be a single instruction, or many instructions, and may even be distributed over several different code segments, among different applications, and across several memory devices. Similarly, operational data may be identified and illustrated herein within the tool, and may be embodied in any suitable form and organized within any suitable type of data structure. The operational data may be collected as a single dataset, or may be distributed over different locations including over different storage devices, and may exist, at least partially, as electronic signals on a system or network.

Furthermore, the described features, structures, or characteristics may be combined in any suitable manner in one or more embodiments. In the following description, numerous specific details are provided, such as examples of agents, to provide a thorough understanding of the disclosed embodiments. One skilled in the relevant art will recognize, however, that the embodiments can be practiced without one or more of the specific details, or with other methods, components, materials, etc. In other instances, well-known structures, materials, or operations are not shown or described in detail to avoid obscuring aspects of the embodiments.

The corresponding structures, materials, acts, and equivalents of all means or step plus function elements in the claims below are intended to include any structure, material, or act for performing the function in combination with other claimed elements as specifically claimed. The description of the present embodiments have been presented for purposes of illustration and description, but is not intended to be exhaustive or limited to the embodiments in the form disclosed. Many modifications and variations will be apparent to those of ordinary skill in the art without departing from the scope and spirit of the embodiments. The embodiment was chosen and described in order to best explain the principles of the embodiments and the practical application, and to enable others of ordinary skill in the art to understand the embodiments for various embodiments with various modifications as are suited to the particular use contemplated. Accordingly, the implementation interpreting a series of images acquired from a subject over time provides a diagnosis based on the interpretation.

It will be appreciated that, although specific embodiments have been described herein for purposes of illustration, various modifications may be made without departing from the spirit and scope of the embodiments. In particular, the number of images, points on a graph, data storages, and comparisons should not be considered limiting. In one embodiment, the Image Diagnostic Tool can be located on a different computer system than the data storage and the system acquiring the image. Accordingly, the scope of protection of these embodiments is limited only by the following claims and their equivalents.

What is claimed is:

1. A computer system comprising:
   a processor in communication with a memory;
   an image capture device operatively coupled to the processor, the device to capture a first image;
   an image diagnostic tool to determine a diagnosis, the image diagnostic tool including program instructions to:
   recognize a morphological feature of an element within the captured first image;
   perform a first comparison including compare the recognized morphological feature to a previously recognized morphological feature of the element within at least one image;
   determine a first probability based on the performed first comparison;
   create a first diagnosis based on the performed first comparison and determined first probability; and
   convert the first captured image to a first diagnostic image, the conversion utilizing the recognized morphological feature, created first diagnosis and determined first probability, and the first diagnostic image being a first visual representation of the created first diagnosis.

2. The system of claim 1, further comprising the image diagnostic tool to:
   capture a second image;
   recognize the morphological feature of the element within the second image;
   perform a second comparison including compare the recognized morphological feature of the second captured image to at least one previously recognized morphological feature of the element within at least one image;
   determine a second probability based on the performed second comparison;
   create a second diagnosis based on the performed first and second comparisons and the determined first and second probabilities; and
   convert the first and second captured images to a second diagnostic image; the convert utilizing the recognized morphological feature, created second diagnosis and determined second probability, and the second diagnostic image being a second visual representation of the created second diagnosis.

3. The system of claim 2, further comprising the image diagnostic tool to:
   determine a change between the recognized morphological feature of the element within the first captured image and the recognized morphological feature within the second captured image;
   perform a third comparison including compare the determined change to a previously determined change of the recognized morphological feature of the element;
   determine a third probability based on the performed third comparison; and
   create a third diagnosis based on the performed third comparison.

4. The system of claim 2, further comprising the image diagnostic tool to:
   recalculate the determined first probability based on the created second diagnosis;
   create a polyline based on the first and second captured images, and recalculated first and determined second probabilities; and
   create a polyline diagnosis based on the polyline.

5. The system of claim 1, wherein the recognition of the morphological feature within the first captured image includes the image diagnostic tool to:
   determine a parameter of a candidate morphological feature within the first captured image;
   perform a second comparison including compare the parameter of the candidate morphological feature to a prior parameter of a previously recognized morphological feature parameter of an element within at least one image; and
   determine the candidate morphological feature is the recognized morphological feature based on the performed second comparison.

6. The system of claim 1, further comprising the image diagnostic tool to:
   determine one or more parameters of a first subject; and
   wherein the performed first comparison includes compare the recognized morphological feature to a previously recognized morphological feature of the element of at least one previous subject having one or more similar parameters to the first subject.

7. The system of claim 1, wherein the morphological feature is selected from the group consisting of: edge, size, shape, and color.

8. A computer program product for determining a diagnosis, the computer program product comprising a computer readable hardware storage device having program code embodied therewith, the program code executable by a processor to:
- capture a first image;
- recognize a morphological feature of an element within the first captured image;
- perform a first comparison including compare the recognized morphological feature to a previously recognized morphological feature of the element within at least one image;
- determine a first probability based on the performed first comparison;
- create a first diagnosis based on the performed first comparison and determined first probability; and
- convert the first captured image to a first diagnostic image, the conversion utilizing the recognized morphological feature, created first diagnosis and determined first probability, and the first diagnostic image being a first visual representation of the created first diagnosis.

9. The computer program product of claim 8, further comprising program code to:
- capture a second image;
- recognize the morphological feature of the element within the second image;
- perform a second comparison including compare the recognized morphological feature of the second captured image to at least one previously recognized morphological feature of the element within at least one image;
- determine a second probability based on the performed second comparison;
- create a second diagnosis based on the performed first and second comparisons and the determined first and second probabilities; and
- convert the first and second captured images to a second diagnostic image; the convert utilizing the recognized morphological feature, created second diagnosis and determined second probability, and the second diagnostic image being a second visual representation of the created second diagnosis.

10. The computer program product of claim 9, further comprising program code to:
- determine a change between the recognized morphological feature of the element within the first captured image and the recognized morphological feature within the second captured image;
- perform a third comparison including compare the determined change to a previously determined change of the recognized morphological feature of the element;
- determine a third probability based on the performed third comparison; and
- create a third diagnosis based on the performed third comparison.

11. The computer program product of claim 9, further comprising program code to:
- recalculate the determined first probability based on the created second diagnosis;
- create a polyline based on the first and second captured images, and recalculated first and determined second probabilities; and
- create a polyline diagnosis based on the polyline.

12. The computer program product of claim 8, wherein the recognition of the morphological feature within the first captured image includes program code to:
- determine a parameter of a candidate morphological feature within the first captured image;
- perform a second comparison including compare the parameter of the candidate morphological feature to a prior parameter of a previously recognized morphological feature parameter of an element within at least one image; and
- determine the candidate morphological feature is the recognized morphological feature based on the performed second comparison.

13. The computer program product of claim 8, further comprising program code to:
- determine one or more parameters of a first subject; and
- wherein the performed first comparison includes compare the recognized morphological feature to a previously recognized morphological feature of the element of at least one previous subject having one or more similar parameters to the first subject.

14. A method for determining a diagnosis comprising:
- capturing a first image;
- recognizing a morphological feature of an element within the first captured image;
- performing a first comparison including comparing the recognized morphological feature to a previously recognized morphological feature of the element within at least one image;
- determining a first probability based on the performed first comparison;
- creating a first diagnosis based on the performed first comparison and determined first probability; and
- converting the first captured image to a first diagnostic image, the converting utilizing the recognized morphological feature, created first diagnosis and determined first probability, and the first diagnostic image being a first visual representation of the created first diagnosis.

15. The method of claim 14, further comprising:
- capturing a second image;
- recognizing the morphological feature of the element within the second image;
- performing a second comparison including comparing the recognized morphological feature of the second captured image to at least one previously recognized morphological feature of the element within at least one image;
- determining a second probability based on the performed second comparison;
- creating a second diagnosis based on the performed first and second comparisons and the determined first and second probabilities; and
- converting the first and second captured images to a second diagnostic image; the converting utilizing the recognized morphological feature, created second diagnosis and determined second probability, and the second diagnostic image being a second visual representation of the created second diagnosis.

16. The method of 15, further comprising:
- determining a change between the recognized morphological feature of the element within the first captured image and the recognized morphological feature within the second captured image;
- performing a third comparison including comparing the determined change to a previously determined change of the recognized morphological feature of the element;

determining a third probability based on the performed third comparison; and creating a third diagnosis based on the performed third comparison.

17. The method of claim 15, further comprising:

recalculating the determined first probability based on the created second diagnosis;

creating a polyline based on the first and second captured images, and recalculated first and determined second probabilities; and creating a polyline diagnosis based on the polyline.

18. The method of claim 14, wherein the recognizing the morphological feature within the first captured image includes:

determining a parameter of a candidate morphological feature within the first captured image;

performing a second comparison including comparing the parameter of the candidate morphological feature to a prior parameter of a previously recognized morphological feature parameter of an element within at least one image; and determining the candidate morphological feature is the recognized morphological feature based on the performed second comparison.

19. The method of claim 14, further comprising:

determining one or more parameters of a first subject; and wherein the performed first comparison includes comparing the recognized morphological feature to a previously recognized morphological feature of the element of at least one previous subject having one or more similar parameters to the first subject.

20. The method of claim 14, wherein the morphological feature is selected from the group consisting of: edge, size, shape, and color.

* * * * *